Figure 1A:
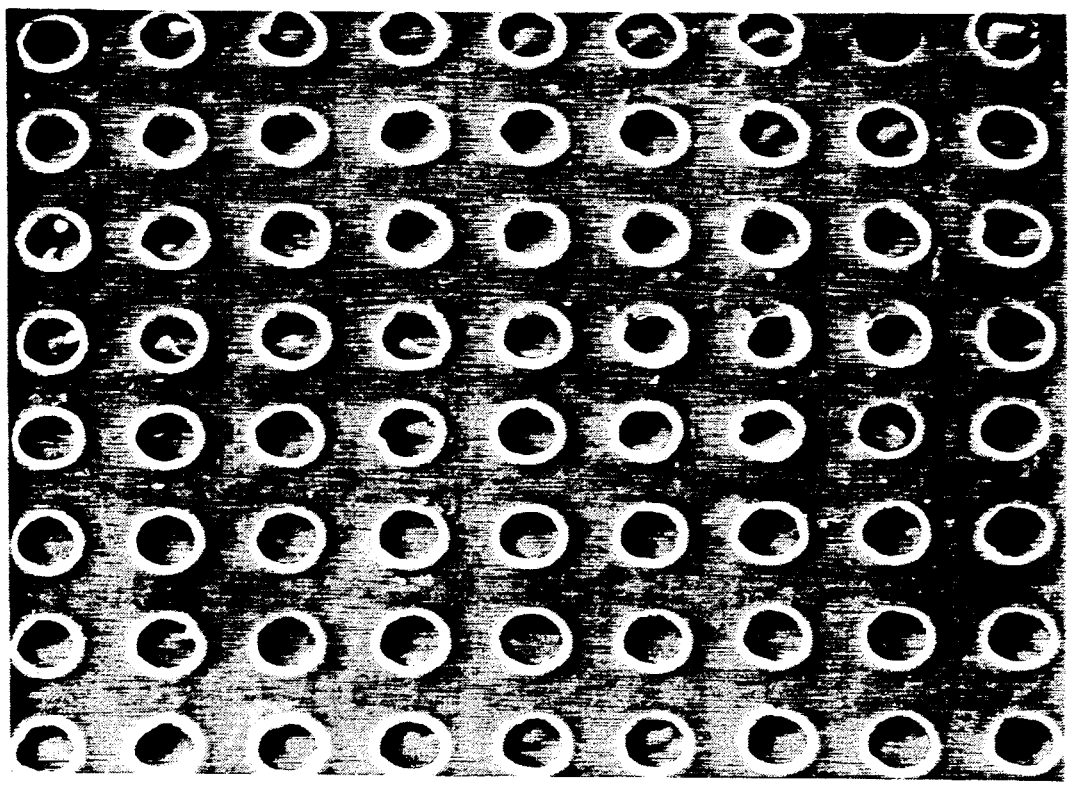

United States Patent [19]

Della Valle et al.

[11] Patent Number: 5,326,356
[45] Date of Patent: Jul. 5, 1994

[54] BIOCOMPATIBLE PERFORATED MEMBRANES, PROCESSES FOR THEIR PREPARATION, THEIR USE AS A SUPPORT IN THE IN VITRO GROWTH OF EPITHELIAL CELLS, THE ARTIFICIAL SKIN OBTAINED IN THIS MANNER, AND ITS USE IN SKIN GRAFTS

[75] Inventors: Francesco Della Valle, Padua; Gabriella Calderini, Carrara San Giorgio; Alessandro Rastrelli, Padua; Aurelio Romeo, Rome, all of Italy

[73] Assignee: Fidia S.p.A., Abano Terme, Italy

[21] Appl. No.: 19,818

[22] Filed: Feb. 16, 1993

Related U.S. Application Data

[63] Continuation of Ser. No. 708,717, May 31, 1991, abandoned.

[30] Foreign Application Priority Data

Jun. 1, 1990 [IT] Italy ................. 20513 A/90

[51] Int. Cl.$^5$ .................. A61F 2/10; A61F 2/02; A61F 2/54; A61F 13/00
[52] U.S. Cl. ........................ 623/15; 623/11; 623/66; 424/422; 424/425
[58] Field of Search .................. 623/15, 66, 1, 11; 128/155, 156; 604/304, 307; 424/447, 448, 422, 423, 424, 425

[56] References Cited

U.S. PATENT DOCUMENTS

| | | |
|---|---|---|
| 2,671,444 | 3/1954 | Pease, Jr. |
| 4,553,272 | 11/1985 | Mears ............................ 623/1 |
| 4,729,766 | 3/1988 | Bergentz et al. ............... 623/1 |
| 4,851,521 | 7/1989 | Della Valle .................. 536/55.1 |
| 4,883,487 | 11/1989 | Yoshizato et al. ............. 623/66 X |

FOREIGN PATENT DOCUMENTS

| | | |
|---|---|---|
| 0183184 | 6/1986 | European Pat. Off. |
| 0351016 | 1/1990 | European Pat. Off. |
| 035806 | 3/1990 | European Pat. Off. |
| 0145600 | 9/1990 | Japan ........................ 623/15 |
| 2178447 | 2/1987 | United Kingdom. |
| 8602273 | 4/1986 | World Int. Prop. O. |
| 8808305 | 11/1988 | World Int. Prop. O. |
| 8903228 | 4/1989 | World Int. Prop. O. |
| 9000595 | 1/1990 | World Int. Prop. O. |

OTHER PUBLICATIONS

George Picha and Dennis Siedlak, "Ion-Beam Microtexturing of Biomaterials" *Medical Device and Diagnostic Industry,* vol. 6, No. 4, Apr. 1984.

*Primary Examiner*—Randall L. Green
*Assistant Examiner*—Dinh X. Nguyen
*Attorney, Agent, or Firm*—Birch, Stewart, Kolasch & Birch

[57] ABSTRACT

It is provided biocompatible membranes constructed of materials of natural, synthetic or semisynthetic origin, and having a thickness of between 10 and 500µ, characterised by containing an ordered series of holes of a constant size between 10 and 1000µ, separated from each other by a constant distance of between 50 and 1000µ, and obtained by perforation by mechanical, thermal laser or ultraviolet radiation means, they being suitable for use as a support for the in vitro growth of epithelial cells. Artificial skins obtained thereby and its use in grafts are also provided.

20 Claims, 7 Drawing Sheets

BIOCOMPATIBLE PERFORATED MEMBRANES, PROCESSES FOR THEIR PREPARATION, THEIR USE AS A SUPPORT IN THE IN VITRO GROWTH OF EPITHELIAL CELLS, THE ARTIFICIAL SKIN OBTAINED IN THIS MANNER, AND ITS USE IN SKIN GRAFTS

This application is a continuation of application Ser. No. 07/708,717 filed on May 31, 1991, now abandoned.

FIELD OF THE INVENTION

This invention relates to new biocompatible perforated membranes, processes for their preparation, their use as a support in the in vitro growth of epithelial cells, artificial skin obtained in this manner, and its use in skin grafts.

PRIOR ART

The loss of cutaneous material for reasons of traumatic or pathological origin is commonly resolved by the autotransplantation technique, using skin explants from donor areas. To cover larger areas these explants can be expanded by surgical methods such as the mesh grafting described by J. Mauchahal, J. Plast. Surgery, 42, 88–91 (1989). These methods give positive results only with small-dimension lesions and patients with a satisfactory general health profile. If elderly patients or those in a state of serious decline are treated, unsatisfactory results are obtained and numerous problems arise, to the extent that such procedures cannot be used. In addition they do not allow a donor tissue expansion of more than 10 times.

An important turning point in the treatment of these lesions by reconstructive surgery was the development of the technique involving the in vitro culture of keratinocytes (J. Rheinwald and H. Green, Cell, 6, 331–344, 1975), which allowed the in vitro expansion of these cultures, to obtain epidermic cell membranes potentially suitable for covering lesion areas.

This technique has been widely used in clinical practice, mostly in the case of patients suffering from burns (G. G. Gallico et al., M. Engl. J. Med., 311, 448–451, 1984), but numerous problems arose from its conception, such as the failure to take of some grafts, the fragility of the epithelial film and the consequent difficulty in its handling by the surgeon, the length of time required for obtaining sufficient quantities of epidermic cultures and the difficulty of obtaining donor areas of sufficient size from patients with large areas of damaged body surface. The in vitro epidermic cultures also require precise orientation to enable the graft to take, this being a particularly risky operation in view of the fragility of in vitro cultivated epidermic film.

A different approach to these problems is described by Yannas et al., Science, 215, 174–176 (1982), who use dermic substitutes in the form of reabsorbable porous materials consisting of coprecipitates of collagen and glycosaminoglycans (GAG), in particular condroitin-6-sulphate, covered by a thin silicone membrane film. The characteristic of these materials is that they comprise non-standardized pores intercommunicating in a manner similar to a sponge.

Zang et al., in Burns, 12, 540–543 (1986) propose a method, known as microskin grafting, consisting of auto-grafting very small skin portions, which then develop to merge into a single epithelium. With this method the maximum donor surface/coverable surface expansion ratio obtainable is 1:15.

S. Boyce and J. Hansborough in Surgery, 103, 421–431 (1988) describe the use of membranes formed from collagen and GAG to promote on their surface the growth of keratinocytes, so reducing the surface porosity of the material. A continuous non-porous layer is also interposed to limit the epidermic culture development to the membrane surface. The possible antigenicity of these dermic substituents, which can result in rejection of the graft, has not yet been properly ascertained.

OBJECT OF THE INVENTION

The object of the present invention is to provide biocompatible membranes which enable in vitro culture of keratinocytes, with culture development in a much shorter time than that previously possible. An important result of the membranes according to this invention is the ability to obtain colonization by homologous or heterologous epithelial cells in a time which is surprisingly short (6–10 days) compared with the time normally required (20–40 days) by traditional methods for preparing comparable areas of in vitro epidermis cultures.

This advantage results in the preparation in a short time of an artificial skin which allows very rapid coverage of an area on which an epithelial transplantation is required, so reducing the risks relating to excessive organic liquid loss or infection.

A further object of the present invention is to provide biocompatible membranes which allow rapid development of keratinocyte cultures with an excellent donor surface/coverable surface ratio, of between 1:20 and 1:200, this being considerably higher than previously obtainable with traditional methods.

A further object of the present invention is to provide a biocompatible and preferably bioreabsorbable artificial skin which can be produced in a short time, is strong, and is easily handled at the moment of transplantation, and which moreover can be applied to the site of the lesion independently of its original orientation in the culture vessel, and can be easily stored. In this respect, an advantage of the artificial skin according to the present invention is that it can be easily cryopreserved to allow the creation of a bank of epithelial tissue, including heterologous. The possibility of cryopreservation also considerably reduces or eliminates, after at least two cycles, the antigenic potential of the surface antigens expressed by the epithelial cells.

DESCRIPTION

These and further objects are attained by the biocompatible membranes according to the present invention, consisting of material of natural, synthetic or semisynthetic origin and having a thickness of between 10 and 500μ, and preferably between 20 and 40μ, characterised by comprising an ordered series of holes of a defined and constant size between 10 and 1000μ, and preferably between 40 and 70μ, separated from each other by a constant distance of between 50 and 1000μ, and preferably 80μ.

These membranes can consist of biocompatible and preferably also bioreabsorbable materials of natural origin such as collagen or coprecipitates of collagen and glycosaminoglycans, cellulose, gelled polysaccharides such as chitin, chitosan, pectins or pectic acids, agar, agarose, xanthan gum, gellan, alginic acid or alginates, polymannans or polyglucans, starches, or natural rubbers, either alone or in mixture with each other or with polymers of synthetic or semisynthetic origin, in the presence of suitable precipitating or gelling agents such as metal salts, polycations or polyanions.

The membranes can also consist of biocompatible and preferably also bioreabsorbable materials of synthetic origin such as polylactic acid, polyglycolic acid or copolymers thereof or their derivatives, polydioxanones, polyphosphazenes, polysulphones or polyurethanes, or semisynthetic derivatives of natural polymers such as collagen crosslinked with crosslinking agents such as dialdehydes or their precursors, bicarboxylic acids or halides thereof, diamines, or derivatives of cellulose, of alginic acid, of starch, of chitin or chitosan, of gellan, of xanthan, of pectins or pectic acids, of polyglucans, of polymannans, of agar, of agarose, of natural rubbers or of glycosaminoglycans.

The membranes can also consist of synthetic polymers, even without the biodegradability characteristic, such as silicone, silane or siloxane rubbers, fluoropolymers such as polyfluoroethylene, polyfluoropropylene, polyfluoroethers, polystyrene, vinyl polychloride, polyacrylate or derivatives thereof, polyhydroxyacrylate, polyhydroxymethacrylate, carboxyvinyl polymers and their derivatives, maleic anhydride polymers and their derivatives, polyvinylchloride, polyvinylalcohol and its derivatives, polyethylene and polypropylene.

The membranes preferably consist of semisynthetic derivatives of hyaluronic acid, in particular ester derivatives thereof such as those described in Examples 6, 7 and 24 of EPA 0216453 filed on 7.7.86, these being biocompatible and biodegradable materials able to release hyaluronic acid on the site of their application, this acid being well known to favour tissue reparative processes. A further characteristic which makes these materials particularly suitable for use according to the present invention is that they do not produce intolerance phenomena, not being immunogenic.

The biocompatible membranes, consisting of one or more of the aforesaid materials have a thickness of between 10 and 500$\mu$ and preferably between 20 and 40$\mu$, and are characterised by the presence of an ordered series of holes of defined and constant size between 10 and 1000$\mu$, and preferably between 40 and 70$\mu$, separated from each other by a constant distance of between 50 and 1000$\mu$, and preferably 80$\mu$.

Continuous biocompatible membranes, consisting of one or more of the aforesaid materials, can be prepared by the conventional methods described in the literature.

The perforated biocompatible membranes according to the present invention are obtained using mechanical perforation devices such as suitably arranged punching machines, or methods involving the use of thermal or ultraviolet lasers operating in a frequency band such as to produce holes of the required size and distance apart in the membrane.

The following example of the preparation of a perforated biocompatible membrane according to the present invention is given by way of illustration only.

EXAMPLE 1

Figure 1B:
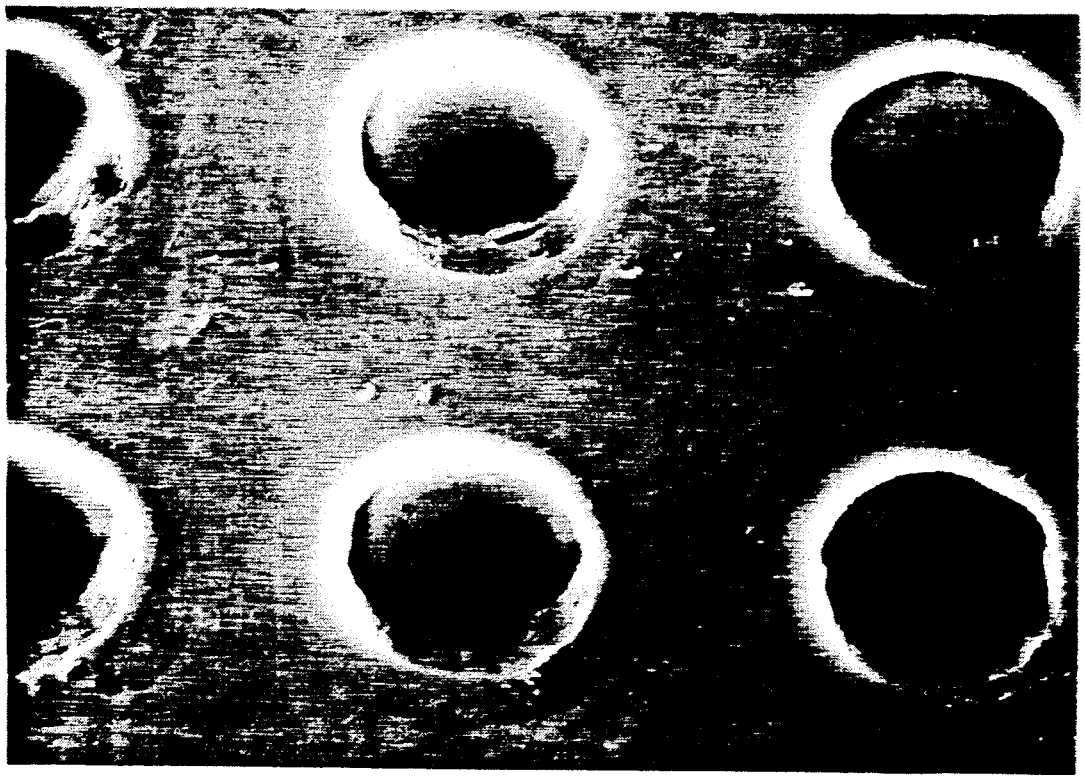

A membrane of hyaluronic acid benzyl ester with 100%, esterification (as described in EPA 0216453 filed on 7.7.86) in the form of a square of 12×12 cm and 25$\mu$ thickness was perforated using a computerized UV Laser device operating at a frequency of 273 $\mu$m under the following operating conditions: working frequency 200 Hz, output energy 250 mJ. Using a suitable screening system, holes having a diameter of 40$\mu$ were obtained at a distance apart of 80$\mu$, as shown in FIGS. 1a and 1b.

The perforated biocompatible membranes according to the present invention can be used advantageously for the in vitro culture of epithelial cells, especially keratinocytes.

For this purpose the membranes can be fixed to the base of cell culture vessels, to metal grids or to any other structure suitable for cell cultures at the air/culture medium interface, using sterile vaselin, sterile silicone or other cementing systems which allow easy removal of the membrane, or by systems involving the use of biological material such as collagen, fibrin or fibrin glue. These membranes can be incubated in culture media suitable for the growth of epithelial cells either alone or in the presence of other cells, such as irradiated fibroblasts, as described in the cited literature, without within the time scheduled for growth and hole colonization causing alteration in mechanical properties which would compromise their handleability and strength within the particular application.

Some of the tests carried out are described below to illustrate the use of the membranes of the present invention.

EXAMPLE 2

The following test was conducted to demonstrate the absence of any inhibition by hyaluronic acid derivative membranes on the in vitro growth of human keratinocyte cell cultures.

Membranes denominated HYAFF 11 cut sterilely into 2×2 cm squares and consisting of hyaluronic acid benzyl ester with 100%, esterification (as described in EP 0216453 filed on 7.7.86) were applied to the base of the culture vessels by means of sterile silicone.

$2 \times 10^5$ human keratinocytes were seeded onto these in a volume of 0.5 ml, in the presence of $4 \times 10^5$ lethally irradiated 3T3 fibroblasts at the second passage.

The capsules were incubated at 37° C. for 2 hours in a 5% $CO_2$ atmosphere to allow the cells to attach to the matrix. After this period 5 ml of CEC culture medium (Green H. et al., J. Proc. Nation. Acad. Sci., 76, 5665–5668, 1979) were added and the capsules again incubated. The culture medium was changed every 2 days. The cells were treated with trypsin 9 days after seeding and counted. All experiments were conducted in duplicate.

| RESULTS | | |
|---|---|---|
| | No. of human keratinocytes per plate ($\times 10^{-5}$) | % inhibition |
| Control | 27 | 0% |
| HYAFF 11 membrane | 27 | 0% |

These results show that the biomaterial used has no inhibiting effect on keratinocyte cultures.

EXAMPLE 3

Growth of Human Keratinocytes Using the Perforated Biocompatible Membranes of the Invention, Obtained by the Method Described in Example 1

HYAFF 11 membranes consisting of hyaluronic acid benzyl ester with 100% esterification (as described in EPA 0216453 filed on 7.7.86) in the form of 3×3 cm squares were cemented to the base of 6 cm diameter Petri capsules using sterile vaselin. Lethally irradiated 3T3 fibroblasts were seeded on the membranes to a concentration of 700,000 cells per plate, under the conditions described in Example 2. After adhesion of the 3T3 cells, i.e. after about 24 hours, a cell suspension of human keratinocytes originating from secondary cultures was added at a concentration of 38,000 cells per cm. The culture conditions were analogous to those described in Example 2. The development of the keratinocyte culture was followed daily using a phase contrast microscope. The development of inoculated epithelial cells was observed on the membrane, these having reached confluence 8-10 days after seeding.

Figure 2:
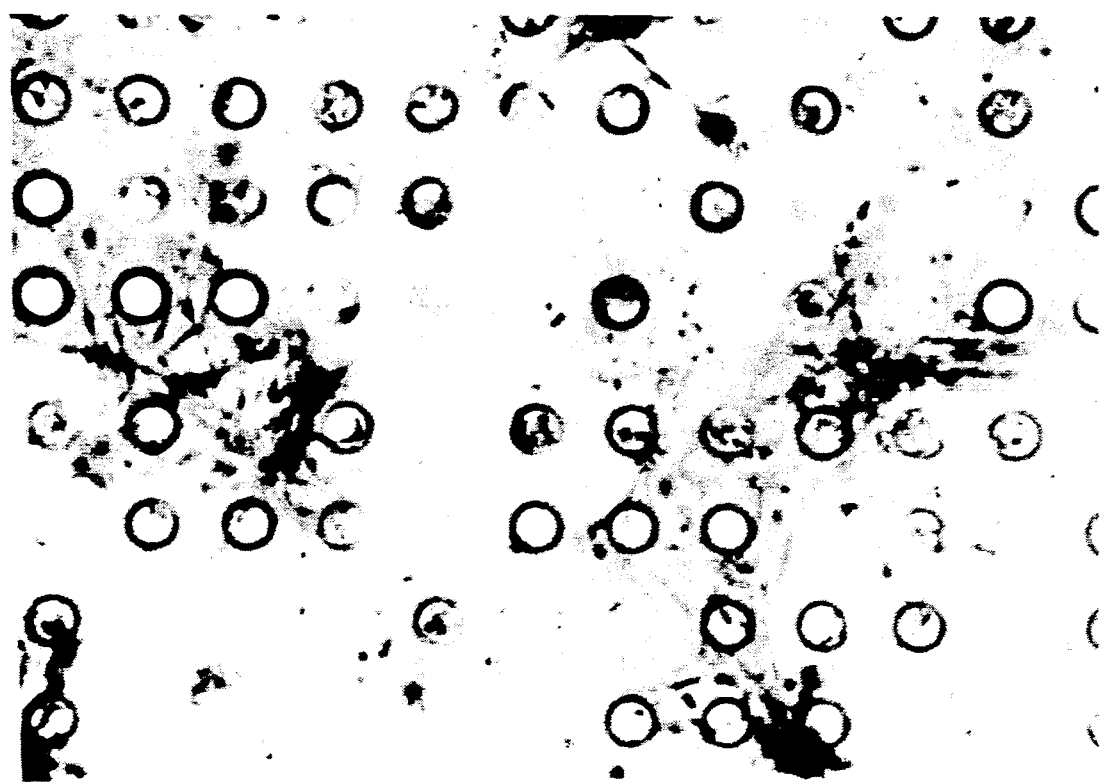
Figure 3:
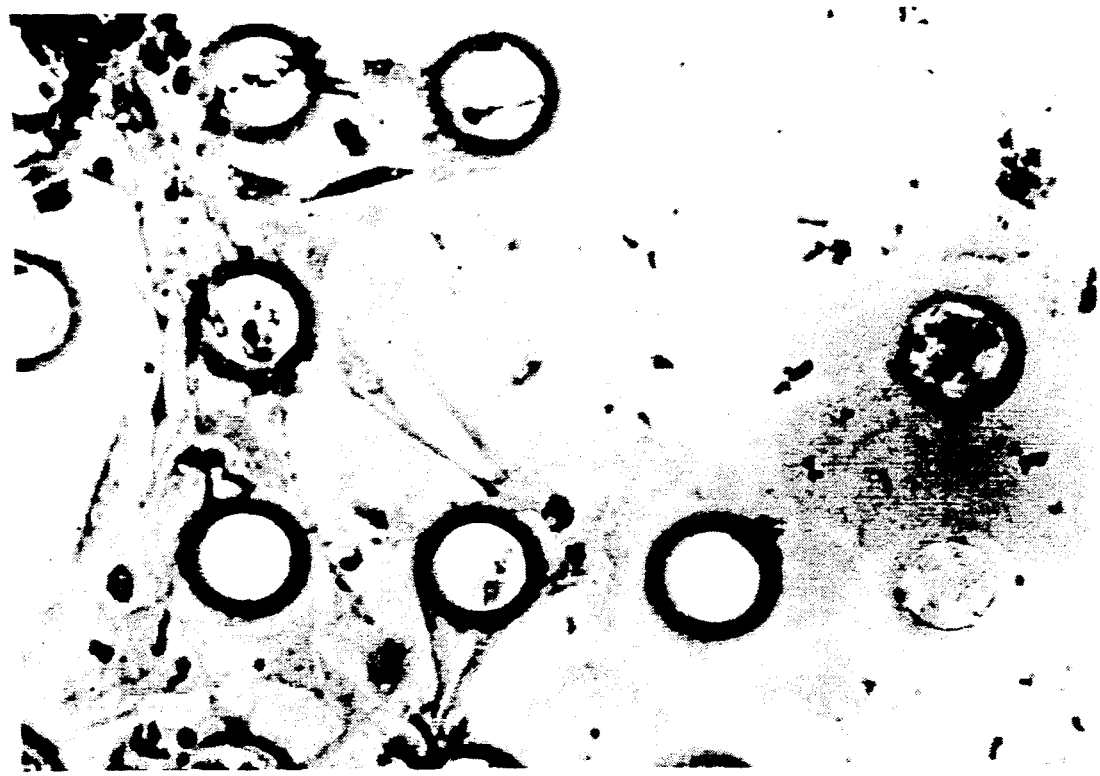
Figure 4:
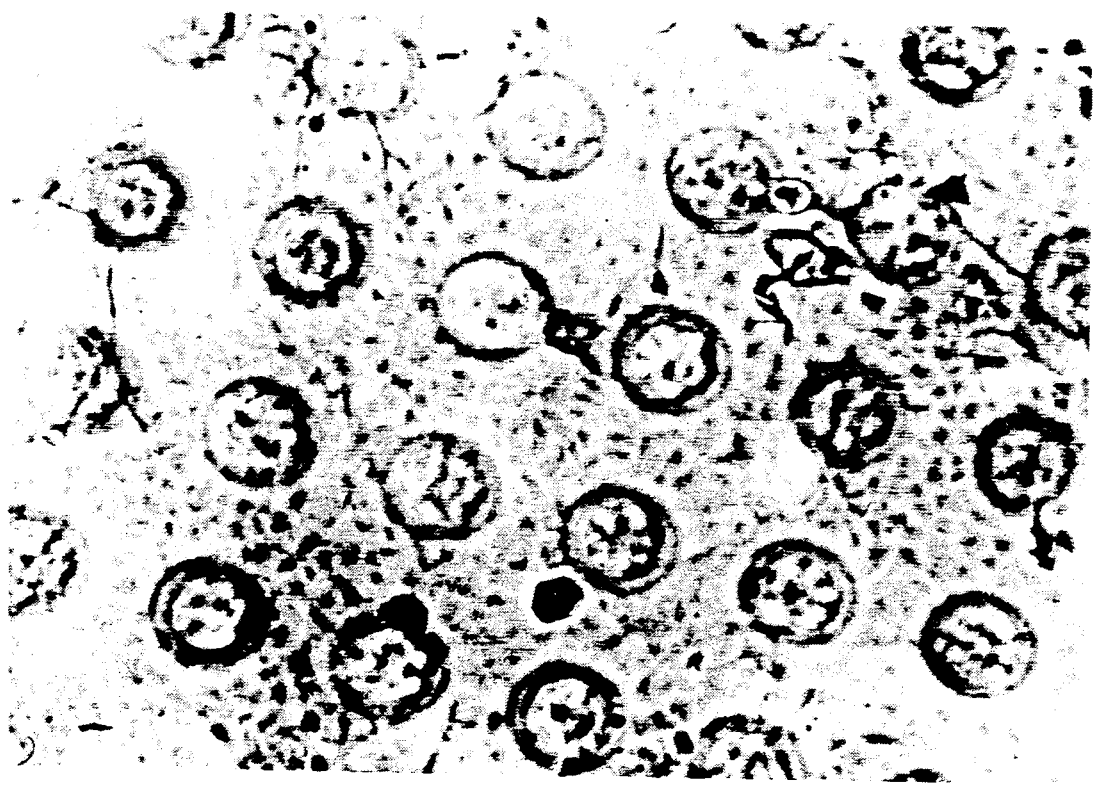

Of particular importance is the fact that even on the second day after seeding, numerous holes contain keratinocytes, their growth being more active within the holes than on the surface, to totally fill them around the 6th day (FIGS. 2, 3 and 4).

Figure 5:
Figure 6:
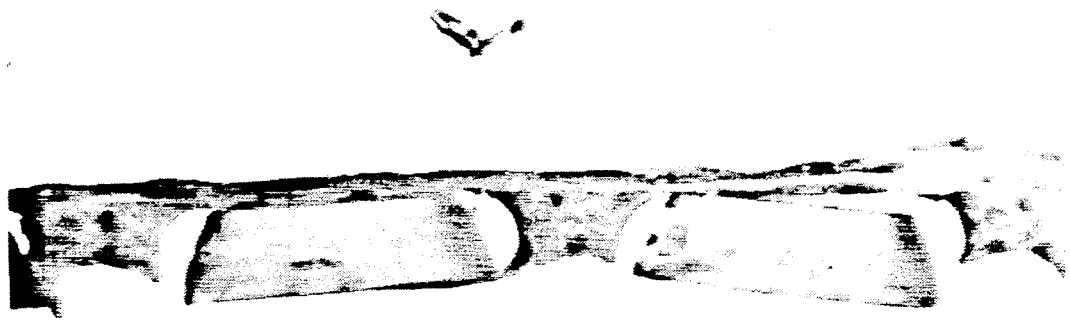

A further fact of great importance is that when analyzed by histological techniques the cells within the holes demonstrate a basaloid appearance documented by the findings of figures showing frequent mitosis (FIGS. 5 and 6), denoting high reproductive vitality. These findings were confirmed by immunohistochemical methods using specific antibodies (Mab).

The epithelial cells grown within the holes can therefore be considered overall to be in the active proliferation stage and thus effectively usable on transplantation areas.

The artificial skin according to the present invention, obtained by the aforesaid procedures, therefore consists of a biocompatible and preferably bioreabsorbable support membrane consisting of materials of natural, synthetic or semisynthetic origin, and having a thickness of between 10 and 500μ, and preferably between 20 and 40μ, characterised by comprising an ordered series of holes of a defined and constant size between 10 and 1000μ, separated from each other by a constant distance of between 50 and 1000μ, together with autologous or heterologous keratinocyte microcolonies in the active proliferation stage present within the holes.

This artificial skin can be easily shaped by the operator on the basis of the areas to be treated, and has a mechanical strength which enables it to be handled without difficulty and be sutured. Once implanted on the lesion area, the keratinocyte microcolonies create growth nuclei of rapid-growing epithelial tissue, which in a short time completely re-epithelialize the area on which the transplantation has been carried out.

It is used by withdrawing it from the culture vessel, removing all traces of culture medium by a sterile physiological solution and applying it to the area to be treated without needing to pay particular attention to the direction of application, as it is equally effective if applied on either of its two sides, in contrast to traditional keratinocyte cultures.

The artificial skin according to the present invention can be used to cover even extensive lesions of the body surface of traumatic origin such as burns, of surgical origin such as withdrawal areas in plastic surgery, or pathological origin such as stasis ulcers or bedsores.

We claim:

1. Biocompatible membranes consisting of materials of natural, synthetic or semisynthetic original, and having a thickness of between 10 and 500μ, which comprise an ordered series of holes of a defined and constant size between 10 and 1000μ, separated from each other by a constant distance of between 50 and 1000μ, said membrane enabling in vitro culture of keratinocytes within the holes and on both sides of said membrane.

2. Biocompatible membranes as claimed in claim 1, in which the hole size is between 40 and 70μ.

3. Biocompatible membranes as claimed in claim 1, in which the distance between holes is 80μ.

4. Biocompatible membranes as claimed in claim 1, in which the biocompatible material of natural origin is chosen from the group consisting of collagen or coprecipitates of collagen and glycosaminoglycans, cellulose, gelled polysaccharides and natural rubbers, either alone or in mixture with each other or with polymers of synthetic or semisynthetic origin, in the presence of suitable precipitating or gelling agents.

5. The biocompatible membranes according to claim 4 in which the gelled polysaccharides are selected from the group consisting of chitin, chitosan, pectins or pectic acids, agar, agarose, xanthan gum, gellano, alginic acid or alginates, polymannans or polyglucans and starches.

6. Biocompatible membranes as claimed in claim 1, in which the biocomcompatible material of synthetic origin is chosen from the group consisting of polylactic acid, polyglycolic acid or copolymers thereof or their derivatives, polydioxanones, polyphosphazenes, polysulphones and polyurethanes.

7. Biocompatible membranes as claimed in claim 1, in which the biocompatible material of semisynthetic origin is chosen from the group consisting of semisynthetic derivatives of natural polymers crosslinked with crosslinking agents and derivatives of cellulose, of alginic acid, of starch, of hyaluronic acid, of chitin or chitinosan, or gellan, of xanthan, of pectins or pectin acids, of polyglucans, of polymannans, of agar, of agarose, of natural rubbers or of glycosaminoglycans.

8. Biocompatible membranes as claimed in claim 7, in which the biocompatible membrane consists of hyaluronic acid benzyl ester with 100% esterification.

9. The biocompatible membranes according to claim 7 in which the semi-synthetic derivative of a natural polymer is collagen.

10. The biocompatible membranes according to claim 7 in which the crosslinking agent is selected from the group consisting of dialdehydes or their precursors, bicarboxylic acids or derivatives thereof and diamines.

11. The biocompatible membranes according to claim 1 which have a thickness of 20-40μ.

12. Artificial skin composed of a biocompatible support membrane consisting of materials of natural, synthetic or semisynthetic origin, and having a thickness of between 10 and 500μ, which contains an ordered series of holes of a defined and constant size between 10 and 1000μ, separated from each other by a constant distance of between 50 and 1000μ, together with autologous or heterologous keratinocyte microcolonies in the active proliferation stage present within said holes and on both sides of said membrane.

13. Artificial skin as claimed in claim 12, in which the hole size is between 40 and 70μ.

14. Artificial skin as claimed in claim 12, in which the distance between holes is 80μ.

15. Artificial skin as claimed in claim 12, in which the biocompatible material of natural origin is chosen from the group consisting of collagen or coprecipitates of collagen and glycosaminoglycans, cellulose, gelled polysaccharides and natural rubbers, either alone or in mixture with each other or with polymers of synthetic or semisynthetic origin, in the presence of suitable precipitating or gelling agents.

16. Artificial skin as claimed in claim 15 in which the gelled polysaccharides are selected from the group consisting of chitin, chitosan, pectins or petic acids, agar, agarose, xanthan gum, gellano, alginic acid or alginates, polymannans or polyglucans and starches.

17. Artificial skin as claimed in claim 12, in which the biocompatible material of synthetic origin is chosen from the group consisting of polylactic acid, polyglycolic acid or copolymers thereof or their derivatives, polydioxanones, polyphosphazenes, polysulphones and polyurethanes.

18. Artificial skin as claimed in claim 12, in which the biocompatible material of semisynthetic origin is chosen from the group consisting of semisynthetic derivatives of natural polymers crosslinked with crosslinking agents and derivatives of cellulose, of alginic acid, of starch, of hyaluronic acid, of chitin or chitosan, of gellano, of xanthan, of pectins or pectic acids, of polyglucans, of polymannans, of agar, of agarose, of natural rubbers or of glycosaminoglycans.

19. Artificial skin as claimed in claim 18, in which the biocompatible material consists of hyaluronic acid benzyl ester with 100% esterification.

20. Artificial skin according to claim 19 which has a thickness of 20–40$\mu$ and the holes are separated from each other by a constant distance of 80$\mu$.

* * * * *